United States Patent [19]

Nakayama et al.

[11] 4,212,831
[45] Jul. 15, 1980

[54] PROCESS FOR PRODUCING TRIPHENYLPHOSPHINE

[75] Inventors: Yoshiki Nakayama, Shimizu; Kazushige Hirao, Shizuoka; Chihiro Yazawa, Yokohama, all of Japan

[73] Assignee: Ihara Chemical Industry Company, Limited, Tokyo, Japan

[21] Appl. No.: 18,620

[22] Filed: Mar. 8, 1979

[30] Foreign Application Priority Data

Mar. 25, 1978 [JP] Japan ............................ 53-34694

[51] Int. Cl.$^2$ ............................................... C07F 9/50
[52] U.S. Cl. .................................................... 568/17
[58] Field of Search ................................. 260/606.5 P

[56] References Cited

U.S. PATENT DOCUMENTS

| | | | |
|---|---|---|---|
| 3,060,241 | 10/1962 | Rauhut et al. | 260/606.5 P |
| 3,099,690 | 7/1963 | Rauhut et al. | 260/606.5 P |
| 3,099,691 | 7/1963 | Rauhut et al. | 260/606.5 P |
| 3,223,736 | 12/1965 | Hechenbleckner et al. | 260/606.5 P |
| 3,470,254 | 9/1969 | Hechenbleckner et al. | 260/606.5 P |
| 3,499,039 | 3/1970 | Lorenz et al. | 260/606.5 P |
| 3,499,041 | 3/1970 | Tamborski | 260/606.5 P |
| 3,723,536 | 3/1973 | Stuebinger et al. | 260/606.5 P |
| 3,751,481 | 8/1973 | Weinberg | 260/606.5 P |

OTHER PUBLICATIONS

Screttas, et al., J. Org. Chem. 27, pp. 2573-2577 (1962).

Primary Examiner—Helen M. S. Sneed
Attorney, Agent, or Firm—Oblon, Fisher, Spivak, McClelland & Maier

[57] ABSTRACT

Triphenylphosphine is produced by reacting a phenylalkali with a phosphorus trihalide in a solvent.

3 Claims, No Drawings

PROCESS FOR PRODUCING TRIPHENYLPHOSPHINE

BACKGROUND OF THE INVENTION

The present invention relates to a novel process for producing triphenylphosphine.

Triphenylphosphine has been mainly used as a catalyst for an oxo process as well as an intermediate of organic compounds such as phosphine oxide.

It has been known to produce triphenylphosphine by reacting a mixture of chlorobenzene and phosphorous trichloride with sodium in West G.P. No. 1,150,981; West German Unexamined Patent Publication Nos. 1,618,116 and 2,007,535.

Thus, the reaction has been unstable and the reaction inducing period has been long and the yield has been low in the conventional process. Therefore, it has been necessary to react them in the presence of a catalyst. Moreover, in accordance with tests made by the inventors, the yield was varied in a range of 64 to 82% and the purity was varied in a range of 92 to 98% and the reproductivities were inferior (though in one example of the reference, it is stated to be a yield of 90% and a purity of 99%).

SUMMARY OF THE INVENTION

It is an object of the present invention to provide a process for producing triphenylphosphine having high purity in high yield and high reproducibility.

The foregoing and other objects of the present invention have been attained by providing a process for producing triphenylphosphine by reacting a phenylalkali with phosphorus trihalide in a solvent.

DETAILED DESCRIPTION OF THE PREFERRED EMBODIMENTS

Suitable phenylalkalis used in the process of the present invention include phenylsodium, phenylpotassium and phenyllithium.

Suitable phosphorus trihalides used in the process of the present invention include phosphorus trichloride, phosphorus tribromide and phosphorus triiodide.

The solvents used in the reaction are preferably solvents which have not halogen atom in the molecule and are not reactive to an alkali metal. Suitable solvents include aromatic hydrocarbons such as benzene, toluene, xylene and ethylbenzene and aliphatic hydrocarbons such as n-octane, iso-octane, n-heptane and pentane.

A molar ratio of a phenylalkali metal to a phosphorus trihalide is 3 or more, preferably 3 to 4 and a reaction temperature is lower than 50° C. preferably 20° to 30° C. in the process of the present invention. In usual, phosphorus trihalide is added to the phenylalkali metal. After the addition, the reaction temperature is maintained to carry out an aging of the reaction mixture. After the reaction, the slurry of the reaction mixture is filtered and the organic phase is concentrated to obtain the reaction product. The solvent is recovered and reused.

It is preferable to treat the slurry of the reaction mixture with water and to concentrate the organic phase separated in the process in order to shorten the processing time, because a filtration of the slurry of the reaction mixture can be eliminated. The reaction time is depending upon an addition of the phosphorus trihalide. The reaction is an exothermic reaction whereby it is preferable to employ a process adding dropwise the phosphorus trihalide under cooling the reaction system by an outer cooling in order to maintain the reaction temperature to a predetermined temperature. The reaction is preferably in a range of 60 to 90 minutes including about 30 minutes for an aging time.

In the process of the present invention, the phenylalkali metals are used as starting materials. It is possible to obtain triphenylphosphine having high purity in high yield by pulverizing sodium metal in the solvent and adding a halobenzene to the dispersion of fine sodium metal in the solvent and then, adding a phosphorus trihalide. In the latter process, an aromatic hydrocarbon such as benzene, toluene, xylene and ethylbenzene is used since the reaction velocity is low in only aliphatic solvent.

The reactions were carried out by using phenylsodium as the phenylalkali metal; and using phosphorus trichloride as the phosphorus trihalide and varying the ratio, the reaction temperature and the solvent as shown in Table. The results of purities and yields of the products of triphenylphosphine are shown in Table. The aging was carried out at room temperature for 30 minutes.

Table

| Molar ratio $\phi$-Na:-PCl$_3$ | Reaction Temp. (°C.) | Time (min.) | Solvent | Product Purity (%) | Yield (%) |
|---|---|---|---|---|---|
| 3.03:1.00 | 60 | 65 | toluene | 88.3 | 85.4 |
| 3.03:1.00 | 20–30 | 60 | " | 96.8 | 97.5 |
| 3.03:1.00 | 20–30 | 60 | xylene | 96.5 | 98.1 |
| 3.03:1.00 | 20–30 | 60 | toluene + n-octane | 96.4 | 96.7 |
| 3.03:1.00 | 20–30 | 60 | toluene + n-pentane | 95.8 | 97.3 |
| 3.03:1.00 | <10 | 75 | toluene | 94.7 | 95.7 |
| 3.06:1.00 | 20–30 | 60 | " | 96.4 | 97.1 |
| 3.12:1.00 | 20–30 | 60 | " | 96.0 | 97.3 |

Note: Yield(%): based on PCl$_3$

In accordance with the present invention, the phenylalkali metal is reacted with the phosphorus trihalide whereby no catalyst is required to obtain triphenylphosphine having high purity in high yield such as higher than 95% at low temperature such as room temperature in high reproducibility and stability. The advantages of the present invention are remarkable especially in an industrial operation.

The present invention will be further illustrated by certain examples and references which are provided for purposes of illustration only and are not intended to be limiting the present invention.

The yield based on PCl$_3$ is shown.

EXAMPLE 1

In a 500 ml flask equipped with a refluxing condenser, a dispersion of 44.14 g of phenylsodium in 200 ml of toluene, 20.0 g of phosphorus trichloride was added dropwise to the dispersion with stirring for 1 hour. During the addition, the temperature of the mixture was kept at 25° C.±5° C. by an outer cooling. After the addition, the mixture was further stirred for 30 minutes to carry out the aging. The slurry of the reaction mixture was filtered and the separated cake was washed with 50 ml of toluene. The filtrate was combined with the washing solution and the organic phase was concentrated to recover toluene and to obtain 38.02 g of triphenylphosphine having the purity of 96.8% in the yield of 97.5% based on PCl₃.

EXAMPLE 2

In accordance with the process of Example 1, the reaction and aging were carried out. The slurry of the reaction mixture was treated with 200 ml of water and the organic phase was separated and concentrated to recover toluene. As the result, triphenylphosphine having the purity of 95.8% was obtained in the yield of 99.5% based on PCl₃.

EXAMPLE 3

In accordance with the process of Example 1 except using 51.24 g of phenylpotassium as the phenylalkali, the reaction and the separation were carried out to obtain triphenylphosphine having the purity of 95.9% in the yield of 96.6%.

EXAMPLE 4

In accordance with the process of Example 1 except using 44.14 g of phenylsodium as the phenylalkali and using 39.42 g of phosphorus tribromide as the phosphorus trihalide, the reaction and the separation were carried out to obtain triphenylphosphine having the purity of 96.5% in the yield of 97.3%.

EXAMPLE 5

In accordance with the process of Example 1 except using 59.96 g of phosphorus iodide as the phosphorus trihalide, the reaction and the separation were carried out to obtain triphenylphosphine having the purity of 96.7% in the yield of 96.9%.

EXAMPLE 6

In a 500 ml flask equipped with a refluxing condenser, 200 ml of toluene and 23 g of sodium metal were charged and heated at 100° C. in nitrogen gas atmosphere to melt sodium metal. The mixture was thoroughly stirred to disperse sodium metal (average diameter of 15μ). The dispersion was cooled at about 25° C. and 57.0 g of chlorobenzene was added dropwise during 1 hour under maintaining the reaction mixture at 25° C.±5° C. by an outer cooling. The initiation of the reaction was remarkably fast to be the inducing period of about 30 seconds (time from addition to initiation of exothermal reaction). The exothermal reaction was substantially finished after the addition. Then, the resulting phenylsodium was not separated and the reaction mixture was maintained at 25° C.±5° C. by an outer cooling and 22.43 g of phosphorus trichloride was added dropwise during 1 hour to obtain triphenylphosphine. After the addition of phosphorus trichloride, the exothermic reaction was stopped. After the addition, the reaction mixture was stirred for 30 minutes to carry out an aging. The slurry of the reaction mixture was filtered and the cake was washed with 50 ml of toluene and the washing solution was combined with the filtrate and the organic phase was concentrated to recover toluene and to obtain 42.3 g of triphenylphosphine having the purity of 97.5% in the yield of 96.2%.

Reference

In a 500 ml flask equipped with a refluxing condenser, 200 ml of toluene and 23 g of sodium metal were charged and heated at 100° C. in nitrogen gas atmosphere to melt sodium metal. The mixture was thoroughly stirred to disperse sodium metal (average diameter of 15μ). The dispersion was cooled at about 50° C. and a mixture of 57.0 g of chlorobenzene and 22.43 g of phosphorus trichloride was added dropwise during 2 hours under maintaining the reaction mixture at 50° C.±5° C. In the reaction, the inducing period was 45 minutes. The exothermic reaction was stopped 40 minutes after the addition. After the addition, the reaction mixture was stirred for 1 hour to carry out an aging. The slurry of the reaction mixture was filtered and the cake was washed with 50 ml of toluene and the washing solution was combined with the filtrate and the organic phase was concentrated to recover toluene and to obtain 37.4 g of triphenylphosphine having the purity of 96.1% in the yield of 87.3%.

What is claimed is:

1. A process for producing triphenylphosphine which consists of adding a phosphorus trihalide to a dispersion of a phenylalkali in an inert solvent selected from the group consisting of aromatic hydrocarbons, aliphatic hydrocarbons and mixtures thereof; at a temperature lower than 50° C.; wherein the molar ratio of the phenylalkali to the phosphorus trihalide is 3 or more; and wherein said dispersion of a phenylalkali is formed by dispersing an alkali metal in said solvent and then adding a halobenzene to form said phenylalkali dispersion.

2. The process according to claim 1, wherein the molar ratio of the phenylalkali to the phosphorus trihalide is in the range of 3 to 4.

3. The process according to claim 1, wherein the reaction mixture formed by the addition of said phosphorus trihalide to said dispersion of a phenylalkali is subjected to an aging.

* * * * *